Dec. 22, 1942. A. W. EICKMEIER Plant Pat. 560
PLUM TREE
Filed Aug. 3, 1942
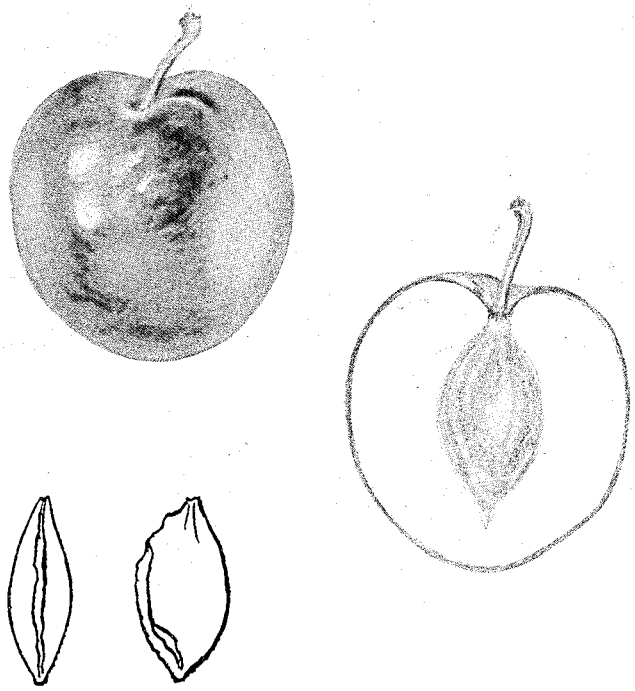
INVENTOR
Andrew William Eickmeier
By Orville M. Kile
PLANT PATENT AGENT Patented Dec. 22, 1942

Plant Pat. 560

UNITED STATES PATENT OFFICE

560

PLUM TREE

Andrew William Eickmeier, Grimsby Beach, Ontario, Canada

Application August 3, 1942, Serial No. 453,406

1 Claim. (Cl. 47—62)

This new discovery relates to a distinct and new variety of plum tree, with particular reference to the fruit produced by the tree.

The new variety is an early-ripening plum with golden flesh and skin of approximately the same basic color which is almost entirely covered by shades of red when mature.

It originated as a chance seedling growing at Grimsby Beach, Ontario, Canada, and I recognized the unusual quality of its fruits as soon as I saw and examined some of them. I have asexually reproduced the variety and quite a stock of young trees has been accumulated.

This new variety somewhat resembles the variety Shiro in growth, foliage and blossoms, although there are some differences such as the fact that my new variety is not so tender to cold and that the leaves of my variety are more sharp-pointed at the apex. Its fruit resembles that of the variety Burbank in shape, texture, flavour and size. But the fruit is a brighter and more intense red than the Burbank when ripe, as well as just before the fully ripe stage. The maturity date is much earlier than either of the above-named varieties. According to records of the Vineland Experiment Station, this new variety ripens 15 days earlier than Shiro, and 24 days earlier than Burbank and my observations show that this is approximately correct.

The firmness of the flesh and the toughness of the skin make this new variety an excellent shipper. It becomes more highly colored just before ripening than do similar varieties, enabling it to be picked in a firmer condition and still be highly colored for marketing. These qualities, together with its early maturity, enable it to cover a wide market at a time when similar plums are absent.

The variety appears to be hardy but tests have not yet been completed.

The original illustrations making up a part of this application show a full side view and a cross-section view of a fully ripened specimen of the fruit of this variety, in approximately their natural colours, together with a view of the seed after removal from the fruit. In the cross-section view the seed appears to be free but that is because it has been scraped.

Following is a description of the tree and its fruit. Colour plate references indicate Ridgway's Color Standards and Nomenclature. Where no plates are indicated, the usual dictionary meaning is intended.

*The tree and blossom*

Growth: Tree large, vigorous, upright-spreading.

Production: Very productive of fruit.

Twigs: Bark mostly smooth; new wood slightly lighter than old; internodes short.

Foliage:

*Arrangement.*—Leaves appear in groups at short irregular intervals along the stem.

*Quantity.*—Abundant.

*Size.*—Largest leaves in a group usually measure about 3 inches in length and about 1¾ inches in width.

*Shape.*—Elliptical to oval, with apex acuminate and base acute. Inclined to fold at midrib. *Margin*—finely and irregularly crenate.

*Texture.*—Medium in weight; somewhat leathery.

*Surface.*—Upper surface glossy; under surface dull and slightly pubescent.

*Veining.*—Prominent; slightly reddish; midrib grooved.

*Glands.*—Numerous small dark glands appear on margin.

*Colour.*—Approximately Elm Green (Pl. XVII) on upper surface, and Light Hellebore Green (Pl. XVII) on under surface.

*Petiole.*—Slender; upper side grooved; lower side smooth; has reddish-brown tinge which continues up midrib of leaf.

Blossoms:

*Borne.*—In clusters on lateral buds. Appear before leaves.

*Size.*—Medium.

*Colour*—White.

*Pedicels.*—Long.

*The fruit*

Maturity: Early, ripening with Earliana and Eickmeier. From 20 to 24 days earlier than Burbank and 12 to 15 days earlier than Shiro.

Form: Globular; halves equal and symmetrical; suture almost indiscernible; cavity shallow; apex usually round but sometimes slightly conic.

Size: Both axial and transverse diameters are approximately 1⅜ inches in an average sized fruit.

Colour: When matured, the clear yellow basic colour is almost entirely overlaid with shades of red ranging from Scarlet to Carmine (Pl. I) and the very slight bloom of this variety permits the colour to show vividly. Almost an entire side of a fully matured specimen is deep Carmine. Minute yellow dots are sometimes found scattered over the surface. When the fruit fully ripens its colour loses some of the scarlet shades and takes on some slight purple tones, as shown in the illustration.

Skin: Glossy; thin but very tough; tart; separates easily from flesh when ripe.

Flesh: Clear deep yellow, approximately Primuline Yellow (Pl. XVI); firm; tender; fine textured; very juicy when ripe. *Flavour*—mostly mild but sour next to seed.

Stone: Clingstone. Irregularly shaped, with sharp points both at stem and apex ends. Ventral suture broad and winged; dorsal suture deep but narrow. Remainder of the surface fairly smooth. *Colour* of seed is approximately Cinnamon-Buff to Cinnamon (Pl. XXIX). *Size*—varies from $\frac{7}{16}$ to ½ inch wide by ¾ to ⅞ inch long.

Stem: Slender; relatively long (½ to ¾ inch); particularly adherent to fruit; light green colour.

Having thus disclosed my discovery, I claim:

The new and distinct variety of plum tree herein described, characterized particularly by its vigorous growth, with its fruit, as shown and described, characterized particularly by its early maturity, its excellent shipping qualities due principally to its firmness of flesh and toughness of skin, and its very deep red surface colour when fully ripe, which surface becomes highly coloured unusually early in its development.

ANDREW WILLIAM EICKMEIER.